United States Patent [19]

Weiss et al.

[11] 4,416,019

[45] Nov. 15, 1983

[54] DEVICE FOR PRODUCING IMAGES OF A LAYER OF AN OBJECT FROM MULTIPLE SHADOW IMAGES WITH VARYING DEGREES OF OVERLAP

[75] Inventors: Hermann Weiss, Duvenstedt; Rolf Linde, Haseldorf; Wilfried Mauser, Hamburg; Erhard Klotz, Halstenbek, all of Fed. Rep. of Germany

[73] Assignee: U.S. Philips Corporation, New York, N.Y.

[21] Appl. No.: 366,126

[22] Filed: Apr. 7, 1982

Related U.S. Application Data

[63] Continuation of Ser. No. 196,416, Oct. 14, 1980, abandoned.

[30] Foreign Application Priority Data

Oct. 12, 1979 [DE] Fed. Rep. of Germany ....... 2941395

[51] Int. Cl.$^3$ ............................................. G03B 41/16
[52] U.S. Cl. ......................................... 378/2; 378/23
[58] Field of Search ................................. 378/2, 21, 23

[56] References Cited

U.S. PATENT DOCUMENTS 3,742,236  6/1973  Richards ............................... 378/23
3,818,220  6/1974  Richards ............................... 378/23
4,078,177  3/1978  Tiemens ............................... 378/23

*Primary Examiner*—Craig E. Church
*Attorney, Agent, or Firm*—Marc D. Schechter

[57] ABSTRACT

The invention relates to a device for producing images of a layer of a three-dimensional object, with radiation sources arranged in a radiation source plane, for irradiating the object with beams of rays from different directions, and with several planar recording layers, arranged parallel to one another, of recording all said shadow images, wherein before each recording layer there is arranged a diaphragm arrangement that has been allocated to it for (stepwise) masking of the beams of rays, and wherein the diaphragm apertures of each diaphragm arrangement are so much the smaller, the greater the distance the diaphragm arrangement is from the radiation sources.

18 Claims, 2 Drawing Figures

U.S. Patent
Nov. 15, 1983
4,416,019
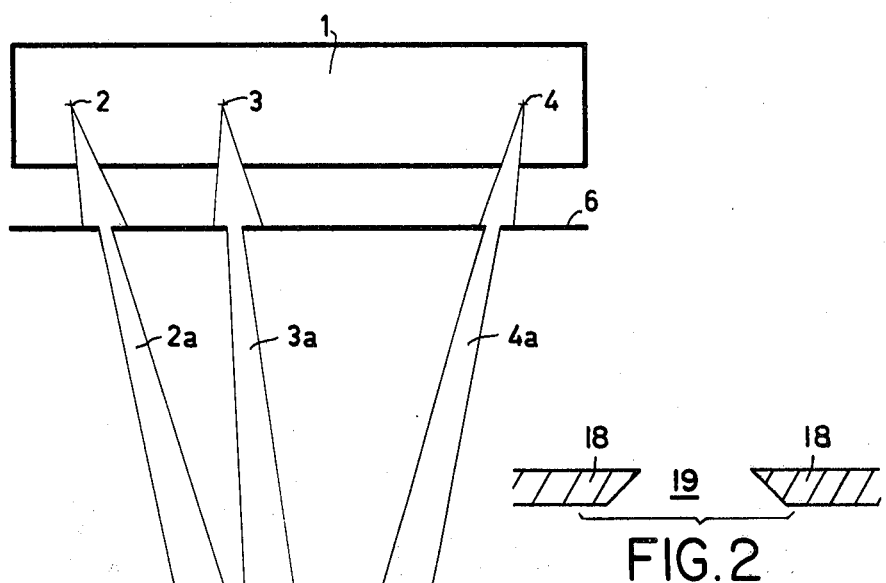
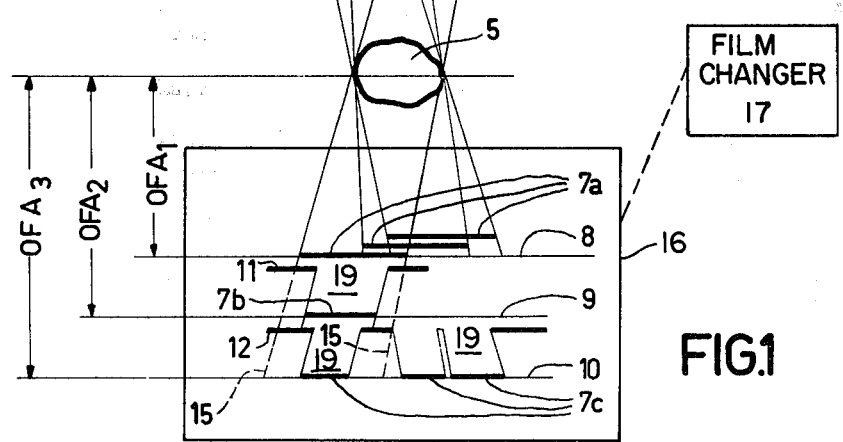
FIG.2
FIG.1

DEVICE FOR PRODUCING IMAGES OF A LAYER OF AN OBJECT FROM MULTIPLE SHADOW IMAGES WITH VARYING DEGREES OF OVERLAP

This is a continuation, of application Ser. No. 196,416, filed Oct. 14, 1980 now abandoned.

The invention relates to a device for producing images of a layer of a three-dimensional object, with radiation sources arranged in a radiation source plane, for irradiating the object with beams of penetrating rays from different directions, and with several planar recording layers, arranged parallel to one another, for the purpose of recording all shadow images thereby generated.

BACKGROUND OF THE INVENTION

In the German Patent application DE-OS No. 25 14 988 there has already been shown, using a multiple radiation sources containing X-ray tubes, how to record coded images on several successive films, the coded images consisting in each case of shadow images superimposed on one another to more or lesser degrees. From these coded images it is possible, in a later step, to reconstruct images of layers of the object (see German patent application DE-OS No. 27 19 386 and 27 46 035).

The images of layers of an object (DE-OS 25 14 988) are obtained in principle from shadow images, but the latter are not present in an isolated but in an overlapped form, then because of this overlap additional artefacts are transferred into the reconstructed image in the process of layer representation and thus impair the picture quality. The influence of the artefacts becomes greater with increasing degree of overlap. The artefacts can in fact be removed; but the method requires multichannel decoding devices for decoding the overlapping shadow images recorded in each of the respective planes. By means of separate shadow images in each recording plane, however, it is possible to avoid the above artefacts and thus considerably improve the image quality. In the case of separate images, however, the object size is severely limited unless film formats that are too big are used. Using a beam geometry that is technically feasible (approximately 25 tubes, focus-object distance FOD = 1200 mm (object-film distance OFA = 500 mm)) and a commercial film format of $40 \times 40$ cm$^2$ it is only possible therefore to record objects with a diameter of approximately 50 mm, separately. In objects of this size, however, it is very difficult for the doctor to make an accurate diagnosis because, with this size, orientation towards adjacent, known and larger object details (for example vessels filled with contrast medium), which can be an important aid to a doctor making his diagnosis, is usually impossible because this information is not present in the images or lies at an unfavourable spot, for example at the edge of the image. It is desirable, therefore, that an image first be prepared of a relatively large object area, which will enable the doctor to orientate himself. An additional exposure, however, means a greater radiation load on the patient. The patient has also to be subjected to more contrast medium if this is being used for exposure purposes. The longer examination period that results is also, of course, a disadvantage for both patient and doctor.

SUMMARY OF THE INVENTION

It is the object of the present invention, therefore, to create a device for producing images of a layer of an object whereby it is possible to prepare both shadow images of large object areas in the case of relatively marked overlap of the shadow images and simultaneously shadow images, which hardly or not overlap, which represent only a part of said large object area. According to the invention the device is characterized in that in front of each recording layer is placed a diaphragm arrangement allocated to it for masking of the beams of rays, the diaphragm apertures of each diaphragm arrangement being so much the smaller the greater the distance between the diaphragm arrangement and the radiation sources.

In this way, the shadow images produced with the multiple radiation source are recorded in a set of films (recording Layers) stacked one above the other in which film by film, the object area and the associated overlap of the shadow images become lesser and lesser.

This means that, when a relatively large object area is irradiated, it is possible to record shadow images of an object on a first film, these shadow images overlapping one another to a large extent but from which it is possible to make an initial diagnosis of the patient. At the same time, without the patient or the object having to be irradiated again, further shadow images of a smaller area of the object are produced which shadow images do not overlap one another or only to a slight extent. From these shadow images it is then possible to reconstruct artefact-free (small) images of a layer of the object. It is important here that the medically relevant object detail should still be present in the masked (thus small) object area.

DESCRIPTION OF THE DRAWINGS

FIG. 1 represents schematically an embodiment of the invention and,

FIG. 2 illustrates in cross section the detail of a diaphragm aperture.

FIG. 1 shows a multiple radiation source 1 with three X-ray tubes 2, 3 and 4. The object 5 is masked with a diaphragm arrangement 6, for example a diaphragm plate. The X-ray beams 2a, 3a, 4a can be restricted in such a way that an area of the object which is irradiated, which is as large as possible, or that the film formats used are fully exposed. The diaphragm 6 can be provided with diaphragm apertures of different or the same size. Diaphragm apertures of a different size can be used, for example, if the shadow images are to be exposed with little overlap and distributed as uniformly as possible over a film. It is also, of course, possible to arrange underneath the object, that is to say between object and first recording layer, a further diaphragm for masking the primary beam of rays (not shown).

The shadow images 7a are recorded on a film 8 at an object-film-distance OFA$_1$. With this distance and with this masked object area the individual shadow images overlap considerably. The result of this is reduced image quality of the reconstructed image of a layer of the object. At the distance OFA$_2$ and OFA$_3$, for example, further films 9 and 10 are simultaneously arranged on which the more strongly masked shadow images 7b and 7c are recorded with the aid of diaphragms (for example lead diaphragms) 11 and 12 arranged between them. For the sake of clarity the full paths of the beams are shown only for radiation source 4. The diaphragm apertures of the diaphragm arrangements 11 and 12 become smaller with increasing object-film distance. In this example, therefore, the perspective images 7c are recorded separately at the distance OFA$_3$. The masking can be done, for example, centrally to the primary beams of rays 2a, 3a, 4a, but also in any other form. Furthermore, the masking may also be different for the individual shadow images, the purpose being always to obtain little or no overlap of the shadow images. Without the diaphragm arrangement 11 and 12 the path of the beam for X-ray source 4 would be as shown with the dashed lines 15.

In this example the object-film distance OFA$_1$ is selected in such a way that the film format of film 8 is utilized to the optimum, i.e. right to the edge. Films 8, 9 and 10 are combined, in a known manner, on both sides with intensifying foils; for the sake of clarity, however, these have not been shown. By suitable adaptation of the intensifier foils (intensification factor) it is possible to ensure that the varying image information (degree of overlap, object-film distance) is recorded on the different films 8, 9 and 10 with approximately the same photographic density. The intensification factor is on a rising scale from 8 to 10. In principle, the adaptation can also be achieved by using X-ray films of different sensitivity. When such a set of films is used, the dose of radiation to with the patient is subjected increases only insubstantially.

Films 7, 8 and 9 are housed, preferably, in a common film cassette 16 (simultaneous cassette) or are simultaneously moved into their respective position by means of a film-changing device 17. FIG. 2 shows a typical aperture 19 in the diaphragms (11 or 12). The thickness of the diaphragm material 18 decreases toward the edges of the aperture, so that the edges of the shadow images will fade out. From the shadow images it is possible, using known decoding methods (DE-AS Nos. 27 19 386 and 27 46 035), to obtain images of layers of the three-dimensional object by means of scale variation and correlation. All the shadow images can be evaluated one after the other with the same decoding device. Rough object orientation is then possible with the layer image reconstructed from the considerably overlapping shadow images 7a, whereas detailed and accurate diagnoses can be made with the layer images reconstructed from shadow images 7b or 7c that have little or no overlap at all. It is assumed, of course, that the desired object detail was also recorded in the set of shadow images present. By means of so-called "survey" exposures, however, that are often made in radiology, it is possible to obtain a rough object orientation for the exposure of the set of shadow images with the multiple radiation source.

What is claimed is:

1. A device for producing images of a layer of a three-dimentional object comprising a plurality of radiation sources arranged in a radiation source plane for irradiating the object with beams of penetrating rays from different directions to generate a plurality of shadow images and a plurality of planar recording layers, arranged parallel to one another at exposure positions, for recording all shadow images thereby generated, characterized in that the device further comprises a plurality of diaphragm means which define apertures disposed between each recording layer and the source plane for masking the beams of rays, wherein the apertures decrease in size as a function of the distance between the associated diaphragm means and the radiation sources.

2. A device as claimed in claim 1, characterized in that each diaphragm means defines apertures of equal size which lie centrally with respect to the beams of rays.

3. A device as claimed in claim 1, characerized in that the diaphragm means define apertures that differ from one another in size, shape and position.

4. A device as claimed in claims 2 or 3, wherein the diaphragm means comprise diaphragm plates.

5. A device as claimed in claim 1, 2 or 3 characterized in that the thickness of the diaphragm means decrease towards the edge of the diaphragm apertures.

6. A device as claimed in claim 4, characterized in that the thickness of the diaphragm means decrease towards the edge of the diaphragm apertures.

7. A device as claimed in claim 1, 2 or 3 further comprising a light-tight cassette which encloses the diaphragm means and the recording layers.

8. A device as claimed in claim 4, further comprising a light-tight cassette which encloses the diaphragm means and the recording layers.

9. A device as claimed in claim 5, further comprising a light-tight cassette which encloses the diaphragm means and the recording layers.

10. A device as claimed in claim 8, further comprising a light-tight cassette which encloses the diaphragm means and the recording layers.

11. A device as claimed in claim 1, 2 or 3 further comprising means which function to position at least the recording layers in their respective exposure positions.

12. A device as claimed in claim 4, further comprising means which function to position at least the recording layers in their respective exposure positions.

13. A device as claimed in claim 5, further comprising means which function to position at least the recording layers in their respective exposure positions.

14. A device as claimed in claim 6, further comprising means which function to position at least the recording layers in their respective exposure positions.

15. A device as claimed in claim 7, further comprising means which function to position at least the recording layers in their respective exposure positions.

16. A device as claimed in claim 8, further comprising means which function to position at least the recording layers in their respective exposure positions.

17. A device as claimed in claim 9, further comprising means which function to position at least the recording layers in their respective exposure positions.

18. A device as claimed in claim 10, further comprising means which function to position at least the recording layers in their respective exposure positions.

* * * * *